(12) United States Patent
Demers

(10) Patent No.: US 7,535,005 B2
(45) Date of Patent: May 19, 2009

(54) PULSED TERAHERTZ SPECTROMETER

(75) Inventor: Joseph R. Demers, Glendale, CA (US)

(73) Assignee: Emcore Corporation, Albuquerque, NM (US)

( * ) Notice: Subject to any disclaimer, the term of this patent is extended or adjusted under 35 U.S.C. 154(b) by 34 days.

(21) Appl. No.: 11/669,685

(22) Filed: Jan. 31, 2007

(65) Prior Publication Data

US 2008/0179527 A1 Jul. 31, 2008

(51) Int. Cl.
*G01J 5/02* (2006.01)
(52) U.S. Cl. .................................. 250/341.1
(58) Field of Classification Search ............... 250/341.1
See application file for complete search history.

(56) References Cited

U.S. PATENT DOCUMENTS

| | | | |
|---|---|---|---|
| 4,594,511 A * | 6/1986 | Cooper et al. | 250/339.07 |
| 5,379,309 A | 1/1995 | Logan, Jr. | |
| 5,623,145 A | 4/1997 | Nuss | |
| 6,304,219 B1 | 10/2001 | Rothe | |
| 6,348,683 B1 | 2/2002 | Verghese et al. | |
| 6,816,647 B1 | 11/2004 | Rudd et al. | |
| 6,844,552 B2 | 1/2005 | Zhang et al. | |
| 6,849,852 B2 | 2/2005 | Williamson | |
| 6,865,014 B2 | 3/2005 | Ciesla et al. | |
| 7,174,037 B2 | 2/2007 | Arnone et al. | |
| 2003/0155512 A1* | 8/2003 | Arnone et al. | 250/341.1 |
| 2006/0255277 A1 | 11/2006 | Cole et al. | |

OTHER PUBLICATIONS

Takeshi Yasui, Yasuhiro Kabetani, Eisuke Saneyoshi, Shuko Yokoyama, Tsutomu Araki, "Terahertz Frequency Comb by Multifrequency-Heterdyning Photoconductive Detection for High-Accuracy, High Resolution Terahertz Spectroscopy", Applied Physics Letters 88, 241104 (pp. 1-3) (2006), American Institute of Physics.

S. Verghese, K.A. McIntosh, S. Calawa, W.F. Dinatale, E.K. Duerr, K.A. Molvar, "Generation and Detection of Coherent Terahertz Waves Using Two Photomixers", Applied Physics Letters, vol. 73, No. 26, 3824-3826, 1998 American Institute of Physics.

Guoqing Chang, Charles J. Divin, Chi-Hung Liu, Steven L. Williamson, Almantas Galvanauskas, Theodore B. Norris, "Power Scalable Compact THz System Based on an Ultrafast Yb-doped Fiber Amplifier", Optics Express, vol. 14, Issue 17, p. 7909-7913, Optics InfoBase, The Optical Society of America.

A. Bartels, F. Hudert, C. Janke, T. Dekorsy, K. Kohler, "Femtosecond Time-Resolved Optical Pump-Probe Spectroscopy at Kilo Rates Over Nanosecond-Time-Delays Without Mechanical Delay Line", Applied Physics Letters, 88, 04117 (2006), Scitation Abstract.

(Continued)

*Primary Examiner*—David P Porta
*Assistant Examiner*—Marcus H Taningco

(57) ABSTRACT

An apparatus for analyzing, identifying or imaging an object including a source of pulsed signals in the range of frequencies from 100 GHz to over 2 THz focused on the object; and a detector for acquiring spectral information from signals reflected from the object and using a heterodyning process to generate an electrical signal representative of some characteristics of the object. The source of pulse signals and the detector is a photoconductive switch activated by a pulsed laser beam.

38 Claims, 5 Drawing Sheets

OTHER PUBLICATIONS

Figure 1:
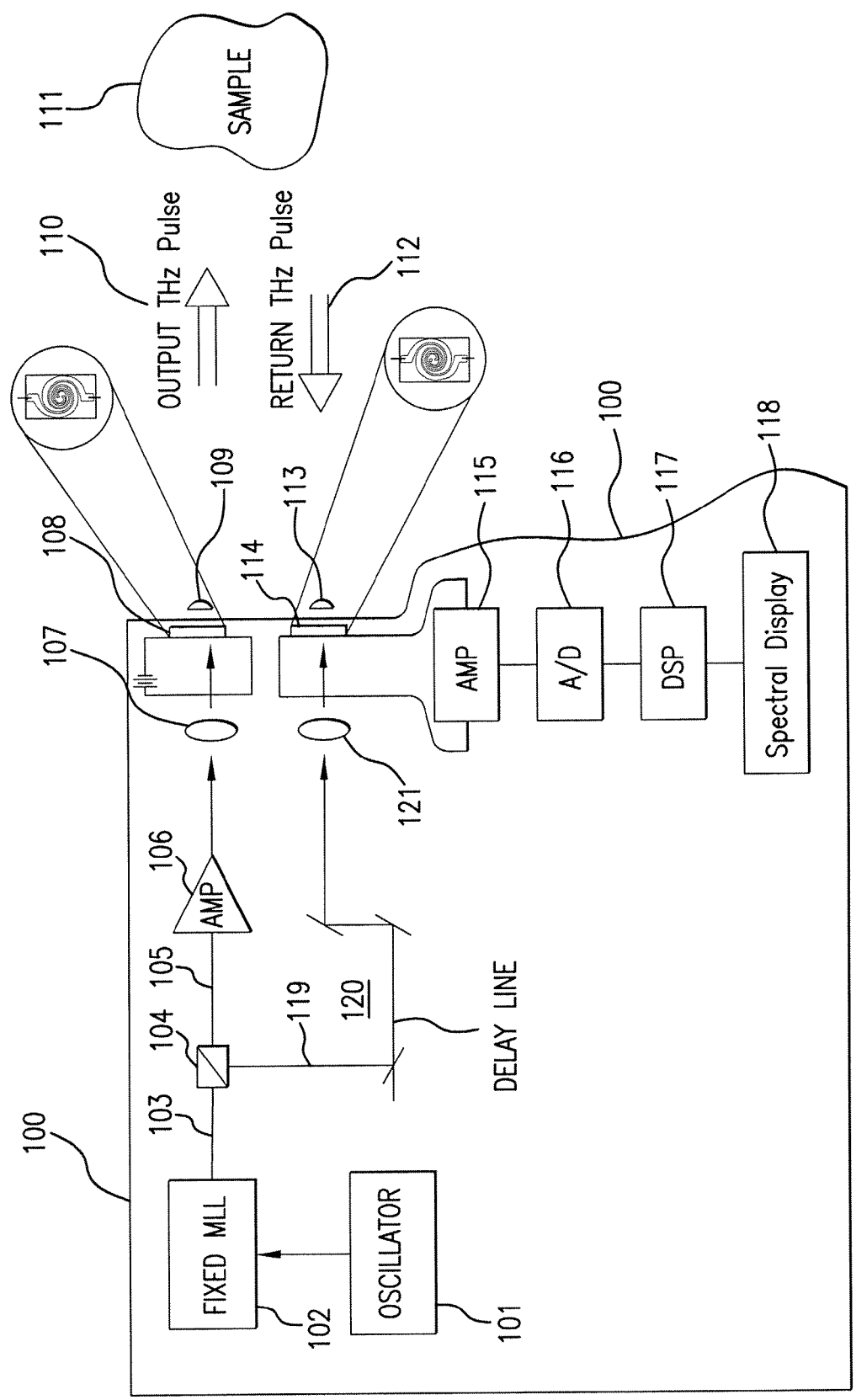

A. Bartels, A. Thoma, C. Janke, T. Dekosry, A. Dreyhaupt, S. Winnerl, M. Helm, "High-Resolution THz Spectrometer with kHz Scan Rates", Optics Express, vol. 14, Issue 1, p. 430-437 (2006), Optics InfoBase, The Optical Society of America.

C. Janke, M. Forst, M. Nagel, H. Kurz, A. Bartels, "Asynchronous Optical Sampling for High-Speed Characterization of Integrated Resonant Terahertz Sensors", Optics Letters, vol. 30, Issue 11, p. 1405-1407 (2005), Optics InfoBase, The Optical Society of America.

Terahertz Measurements of Resonant Planar Antennas Coupled to Low-Temperature-Grown GaAs Photomixers; K.A. McIntosh et al., 1996 American Institute of Physics; pp. 1-4.

Spectroscopic Applications and Frequency Locking of THz Photomixing with Distributed-Bragg-Reflector Diode Lasers In Low-Temperature-Grown GaAs; Pin Chen et al.; 1997 American Institute of Physics; pp. 1601-1603.

Superconductive Hot Electron Mixers with Ultra Wide RF BandWidth for Heterodyne Receiver Applications Up to 3 THz; W. R. McGrath, et al.; Proceedings of the ESA Symposium; p. 15-17; Apr. 1997.

* cited by examiner

PULSED TERAHERTZ SPECTROMETER

BACKGROUND OF THE INVENTION

1. Field of the Invention

The invention relates to microwave, millimeter wave and submillimeter wave sources and in particular to a pulsed heterodyne transceiver useful for terahertz spectroscopy.

2. Description of the Related Art

Terahertz devices and systems generally refer to creating and detecting electromagnetic energy between 300 GHz and 3 terahertz (3 THz), or wavelengths from 100 to 1000 microns (0.1 to 1.0 millimeters), and also referred to as the submillimeter or far-infrared region of the electromagnetic spectrum. Terahertz energy can be created, for example, using short-pulsed lasers, heterodyne lasers, electronic diode multipliers, free-electron lasers, and BWOs.

One important application of terahertz systems is THz spectroscopy, and more particularly realized as time domain spectroscopy. In such systems, a sequence of femtosecond pulses from a mode locked laser are focused onto suitable semiconductor material to produce THz radiation. The radiation is directed to the target or sample to be analyzed, and a detector or detector array is used to collect the signal propagated through or reflected from the object. Since such measurements are made in the time domain by collecting the timed sequence of pulses, the signals must then be processed by a Fourier transformation to recover the frequency domain spectral information.

Terahertz spectroscopy presents many new instrumentation and measurement applications since certain material and objects can be identified and characterized by a frequency-dependent absorption, dispersion, and reflection of terahertz signals which pass through or are reflected from the material object. Some current terahertz systems perform analyses in the time-domain by collecting that transmitted signal propagating through the object and then processing the information contained in those signals by a Fourier transformer to produce a spectral analysis. By scanning every point or "pixel" on that object, either on a focal plane or in successive focal planes at different ranges, it is also possible for such a system to perform imaging of the surface or interior cross-sections or layers of the object. This non-invasive imaging technique is capable of differentiating between different materials, chemical compositions, or molecules in the interior of an object.

As noted in a review article by Peter H. Siegel in, IEEE Transactions on Microwave Theory and Techniques, Vol. 50, NO. 3, 915-917 (March 2002), terahertz time-domain spectroscopy was pioneered by Nuss and others at Bell Laboratories in the mid-1990s (B. B. Hu and M. C. Nuss, "Imaging with terahertz waves," Opt. Lett., vol. 20, no. 16, pp. 1716-1718, Aug. 15, 1995; D. M. Mittleman, R. H. Jacobsen, and M. C. Nuss, "T-ray imaging," IEEE J. Select. Topics Quantum Electron., vol. 2, pp. 679-692, September 1996.), and recently commercialized by at least two companies, Picometrix, LLC of Ann Arbor, Mich. (D. D. Arnone et al., "Applications of terahertz (THz) technology to medical imaging," in Proc. SPIE Terahertz Spectroscopy Applicat. II, vol. 3823, Munich, Germany, 1999, pp. 209-219.) and Teraview Ltd. (a spinoff of Toshiba Research Europe) located in Cambridge, England (D. Arnone, C. Ciesla, and M. Pepper, "Terahertz imaging comes into view," Phys. World, pp. 35-40, April 2000.).

In situ measurements of the transmitted or reflected terahertz energy incident upon a small sample are processed to reveal spectral content (broad signatures only), time of flight data (refractive index determination, amplitude and phase, and sample thickness), and direct signal strength imaging. The principle involves generating and then detecting terahertz electromagnetic transients that are produced in a photoconductor or a crystal by intense femtosecond optical laser pulses. The laser pulses are beam split and synchronized through a scanning optical delay line and made to strike the terahertz generator and detector in known phase coherence. By scanning the delay line and simultaneously gating or sampling the terahertz signals incident on the detector, a time-dependent waveform proportional to the terahertz field amplitude and containing the frequency response of the sample is produced. Scanning either the terahertz generator or the sample itself allows a 2-D image to be built up over time.

Other developments include rapid scanning (S. Hunsche and M. C. Nuss, "Terahertz 'T-ray' tomography," in Proc. SPIE Int. Millimeter SubmillimeterWaves Applicat. IV Conf., San Diego, Calif., July 1998, pp. 426-433.) and true 2-D sampling using charge-coupled device (CCD) arrays (Z. Jiang and X.-C. Zhang, "Terahertz imaging via electrooptic effect," IEEE Trans. Microwave Theory Tech., vol. 47, pp. 2644-2650, December 1999.). In the Picometrix and Lucent Technologies systems, the generator and detector are based on the photoconductive effect in low-temperature- grown (LTG) GaAs or radiation-damaged silicon on sapphire semiconductor. The Teraview system uses terahertz generation by difference frequency mixing in a nonlinear crystal (ZnTe) and detection via the electrooptical Pockels effect (measuring the change in birefringence of ZnTe induced by terahertz fields in the presence of an optical pulse) as first demonstrated by Zhang at the Rensselaer Polytechnic Institute (RPI), Troy, NY (see Q. Wu, T. D. Hewitt, and X.-C. Zhang, "Two-dimensional electro-optic imaging of THz beams," Appl. Phys. Lett., vol. 69,no. 8, pp. 1026-1028, Aug. 19, 1996.). The femtosecond optical pulses are currently derived from relatively expensive Ti: Sapphire lasers, but other proposals include longer wavelength, especially 1.5 m, solid-state systems that can take better advantage of fiber technology (Mittleman). The RF signals produced by the optical pulses typically peak in the 0.5-2 THz range and have average power levels in the microwatt range and peak energies around a femtojoule. This makes T-ray imaging a very attractive tool for the medical community (noninvasive sampling), as well as for nondestructive probing of biological materials or electronic parts. The technique is rapidly gaining an enormous following and is poised to be an exploding commercial success once the system can be made less costly (replacement of the Ti: sapphire laser with solid-state devices), faster (through 2-D imaging techniques) and somewhat more sensitive (with better sources and detectors). The largest drawback is the need to scan the delay line slowly and over a distance of the desired wavelength resolution (e.g., a 1 GHz resolution would require a 7.5 cm scan).

The need for a multi-octave tunable spectrometer in the THz region is justified by the new suite of applications relating to materials identification facing researchers and system developers today. Historically, the THz field has been dominated by radio astronomers and chemists usually aimed at detecting trace amounts of small gaseous molecules in the interstellar medium or in the Earth's upper atmosphere. The low pressure of the media involved would often lead to narrow, Doppler-limited absorption lines, sometimes less than 1 MHz in linewidth. In roughly the last decade, the THz landscape has changed dramatically with the discovery and demand for detection and imaging of larger molecules, particularly biomolecules and bioparticles. This includes, for example, proteins and vitamins using frequency sweeps above 1 THz, and bacterial spores and nucleic acids using frequency sweeps below 1 THz. In all cases the biomolecular and bioparticle absorption occurs not in the form of narrow lines, but rather as broad "signatures", typically 1 to 10 GHz or wider. A good example of a bioparticle of current research interest would be the spores of *Bacillus subtilus* (an Anthrax surrogate), which have recently displayed approximately 6 GHz broad signatures centered around 260 and 420 GHz. In addition, these signatures tend to have less maximum absorption strength than their small molecular counterparts, making them more difficult to "specify" against background noise, standing waves, and other spurious effects. A multi-octave spectrometer allows measurement of two or more signatures in the same session, increasing confidence and specificity.

In addition to the time-domain spectrometers noted above, frequency domain systems are also known (See the paper by Verghese et al., "Generation and detection of coherent terahertz waves using two photomixers," Appl. Phys. Lett., vol. 73, no. 26, pp. 3824-3826, Dec. 28, 1998.). One prior art terahertz spectrometer system is described in U.S. patent application Ser. No. 11/121,350, assigned to the common assignee, and hereby incorporated by reference. The system includes a laser illumination arrangement that generates a pair of source laser beams incident on a source photomixer device or photoconductive switch (PCS) to cause emission of subcentimeter radiation, at least a portion of which interacts with the remote sample to generate a "sample influenced radiation" which is then incident on a detector photomixer device. A second pair of laser beams is incident on the detector to produce an optical component of the detector photocurrent that is offset in frequency with respect to the detected source laser energy. As a result, the detector generates a frequency down-converted electrical output signal responsive to and characteristic of the sample influenced radiation.

Some of the limitations of such prior art systems are the long sweep time required to perform scans, limited frequency range of PCS less than or equal to 2 THz, the difficulty in providing multiple lasers with a high degree of timing accuracy, and mechanical beam alignment issues.

Prior to the present invention, there has not been an implementation of terahertz spectrometer that is small, portable, and low cost and suitable for field or portable use and applications.

SUMMARY OF THE INVENTION

1. Objects of the Invention

It is an object of the present invention to provide an improved terahertz spectrometer.

It is another object of the present invention to provide a terahertz pulse comb system for the identification of a target.

It is also another object of the present invention to provide a pulsed heterodyne receiver for a terahertz system.

It is still another object of the present invention to provide a field portable terahertz system capable of identifying or imaging an object.

Additional objects, advantages, and novel features of the present invention will become apparent to those skilled in the art from this disclosure, including the following detailed description as well as by practice of the invention. While the invention is described below with reference to preferred embodiments, it should be understood that the invention is not limited thereto. Those of ordinary skill in the art having access to the teachings herein will recognize additional applications modifications and embodiments in other fields, which are within the scope of the invention as disclosed and claimed herein and with respect to which the invention could be of utility.

BRIEF DESCRIPTION OF THE DRAWINGS

These and other features and advantages of this invention will be better understood and more fully appreciated by reference to the following detailed description when considered in conjunction with the accompanying drawings wherein:

FIG. 1 is a block diagram of a time domain terahertz spectrometer known in the prior art;

FIG. 2 is a block diagram of the terahertz spectrometer according to the present invention;

FIG. 3A is a graph illustrating the optical frequency spectrum obtained upon high-speed photodetection of the first mode-locked laser in the spectrometer of FIG. 2;

FIG. 3B is a graph illustrating the optical frequency spectrum obtained upon high-speed photodetection of the second mode-locked laser in the spectrometer of FIG. 2;

FIG. 3C is a graph illustrating the absorption spectrum of a sample plotted over the frequency spectra of the emitted terahertz RF beam from the photoconductive switch according to the present invention;

FIG. 3D is a graph illustrating the frequency spectra of the received terahertz RF beam at the detector photoconductive switch according to the present invention; and FIG. 3E is a graph illustrating the downconverted spectra in the RF domain.

The novel features and characteristics of the invention are set forth in the appended claims. The invention itself, however, as well as other features and advantages thereof, will be best understood by reference to a detailed description of a specific embodiment, when read in conjunction with the accompanying drawings.

DETAILED DESCRIPTION OF THE PREFERRED EMBODIMENT

Details of the present invention will now be described, including exemplary aspects and embodiments thereof. Referring to the drawings and the following description, like reference numbers are used to identify like or functionally similar elements, and are intended to illustrate major features of exemplary embodiments in a highly simplified diagrammatic manner. Moreover, the drawings are not intended to depict every feature of actual embodiments or the relative dimensions of the depicted elements, and are not drawn to scale.

As noted above, terahertz spectrometer systems may be either frequency domain or time domain systems. FIG. 1 is a block diagram that depicts a typical terahertz time domain spectrometer 100 according to the prior art. The spectrometer includes a source of repetitive, electrical pulses from a crystal oscillator 101 which drives a fiber mode-locked laser (MLL) 102, such as a 780 nm laser manufactured by Calmar Optcom Inc. of Sunnyvale, Calif. Such a laser is mode locked by means of active modulation of the laser gain at a cavity resonance. The output beam 103 of such a mode locked laser is a sequence of pulses, each pulse having a time duration of less than 1 picoseconds and spaced 10 nanoseconds apart (i.e., a pulse repetition rate of 100 MHz). The output beam 103 of the laser is coupled by free space propagation to beam splitter 104 to create two paths: one path 105 being applied to an optical amplifier 106, and a second path 119 being applied to a scanning delay line 120. The amplifier 106 is typically a tapered amplifier such as a model TEC-400 manufactured by Sacher Lasertech of Marburg, Germany, which boosts the power level of the beam 105, typically 2-3 mW (joules/milliwatts) to a power level of 100 mW. The output of the amplifier 106 is coupled by free space propagation to a lens 107, which focuses the beam on a low-temperature-grown (LTG) gallium arsenide (GaAs) photoconductive switch (PCS) semiconductor device 108. The PCS is biased by a battery or other power source.

The femtosecond optical pulses have a spot size about ten microns on the surface of the semiconductor PCS device 108, which produces terahertz radiation in the frequency range from 100 GHz to over 2 THz. The radiation from the PCS device is focused by a hemispherically shaped silicon lens 109 closely adjacent thereto, and which is approximately two or three centimeters in diameter. The antenna structure of the PCS device 108 functions to couple the THz pulses into free space radiation.

The outgoing terahertz radiation beam 110 is relatively low power, about 1 microwatt at 1 THz. The target or sample object 111 in the path of the beam to be analyzed by the spectrometer will absorb some radiation and reflect a portion of the radiation back in the direction of the source or user, as depicted by return THz pulse 112. The useful range may also be affected by atmospheric conditions.

Turning to the receive side of the prior art time domain spectrometer 100, the optical beam output of the scanning delay line 120 is applied to a focusing lens 121 which is then directed to the surface of a second LTG PCS device 114. A hemispherical lens 113 and a time-gated detector or detector array is provided. The detector includes a receiving antenna which is implemented as a LTG PCS semiconductor device 114 similar to the transmitting device 108, except as noted in the Figure, oriented in a different direction. An adjustable scanning delay line for changing the delay between the femtosecond pulses on the transmitter and the gating pulses on the detector at a rate of a few Hertz to hundreds of Hertz for the purpose of temporally heterodyning the THz-frequency transits down into the acoustic (Hz) range so that they can be processed electronically. The PCS device 114 is coupled to a transimpedance amplifier 115, which produces an analog output signal which is coupled to an analog to digital converter 116, which is followed by a digital signal processing unit 117. The digital signal processor processes the time-domain data and extracts the desired information, which may then be recorded, printed or displayed for the image or data associated with the target on display.

In typical prior art applications, the object to be investigated is located at a distance of one foot from the spectrometer. It is known that specific chemical compounds and molecules in certain material and objects can be identified or characterized by a frequency-dependent absorption, dispersion, and reflection of terahertz transient signals as the pulsed terahertz radiation passes through the material or object. The spectrometer 100 analyzes that frequency dependence in the time domain by collecting that transmitted signal propagating through the object and then processing the information contained in those signals or from a region or "pixel" on that object. The frequency response presents a signature or frequency spectrum capable of differentiating between different materials, chemical compositions, or molecules in the target.

A typical prior art terahertz transmitter emits electromagnetic radiation after being illuminated by a 100 fs laser pulse from either a modelocked dye laser operating around 620 nm or a modelocked Ti: Sapphire or CR:LiSaF laser operating around 800 nm. Because of the short duration of the THz-transient, the spectrum is broadband, typically extending thousands of GHz.

One of the limitations of such prior art designs is that it is important that there is a high degree of correlation between the phase fluctuations of two independent single frequency lasers, which are operating at two slightly different optical frequencies, which is difficult to attain in practice.

Figure 2:
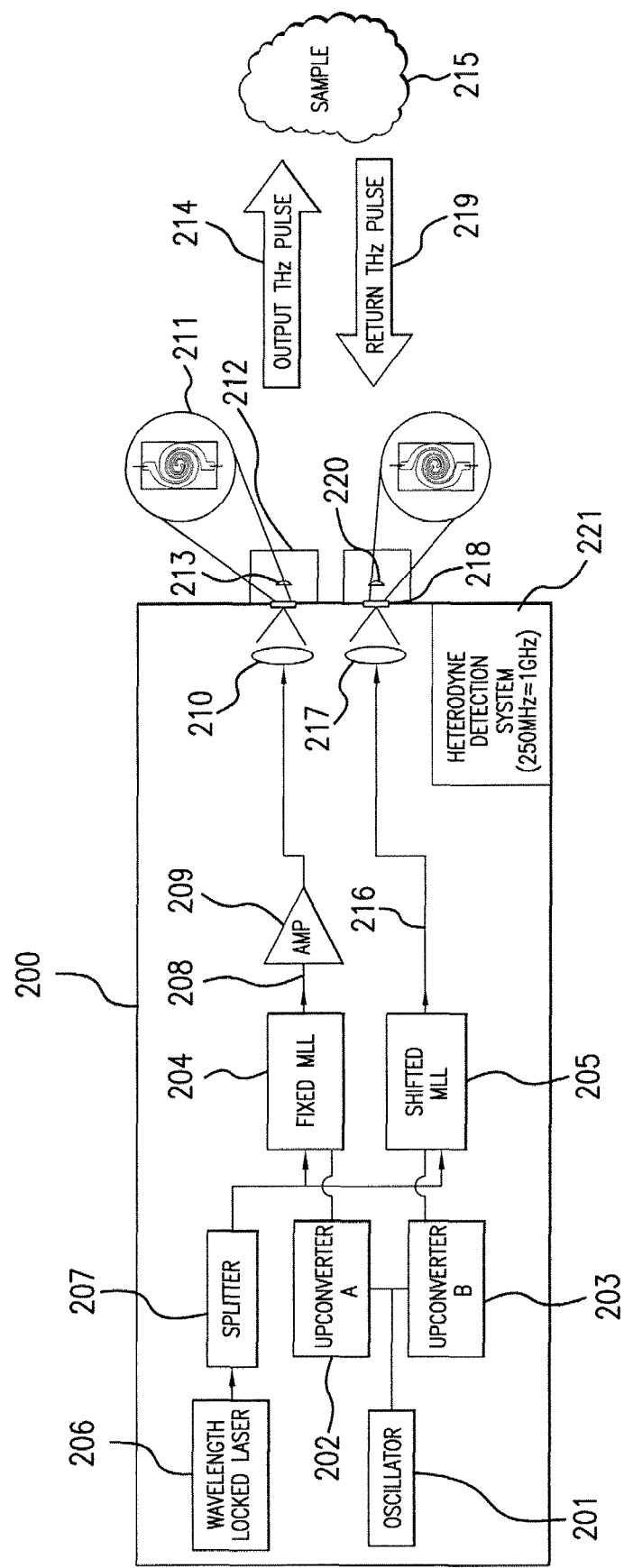
Figure 3A:
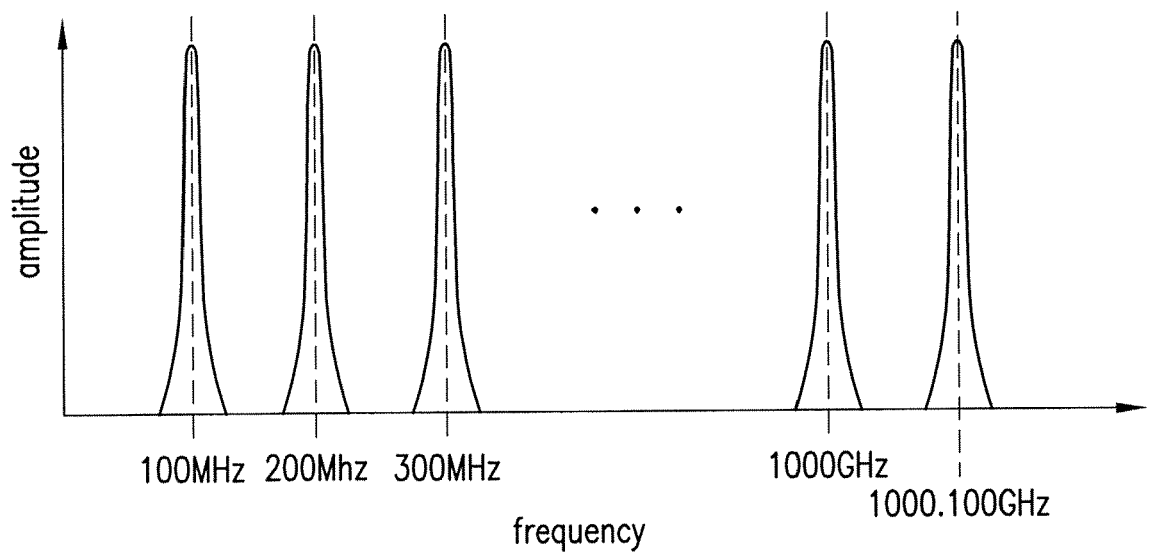
Figure 3B:
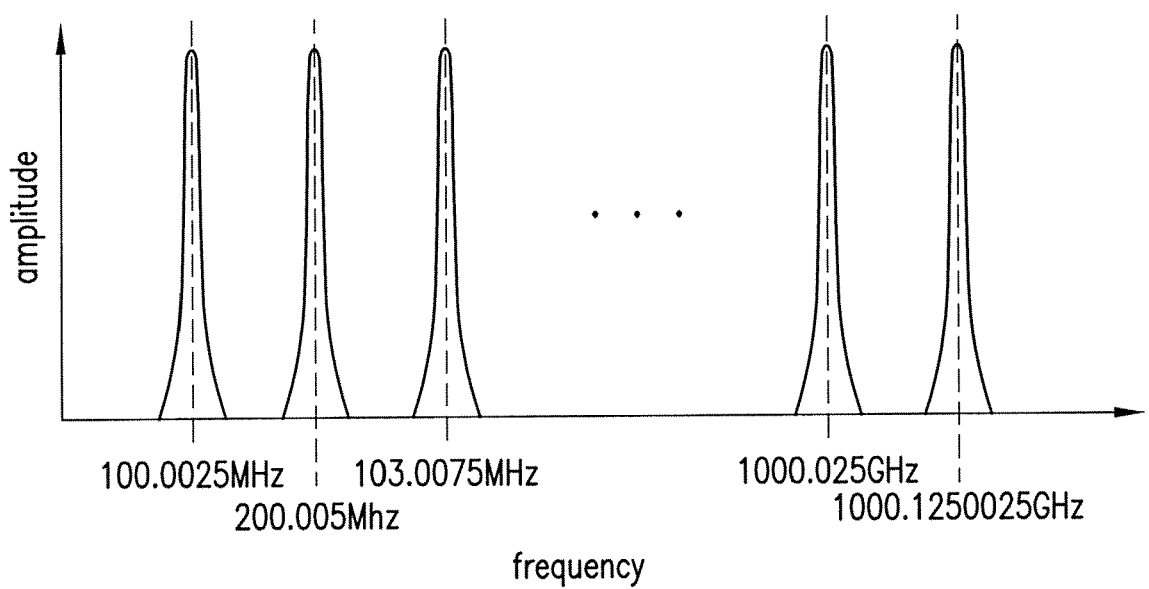

The spectrometer of the present invention is depicted in the block diagram of FIG. 2, which depicts a housing 200, suited for portable use in the field. A crystal oscillator 201 produces a 10 MHz sine wave which drives an upconverter (frequency multiplier) 202 and frequency synthesizer 203 whose output is applied to a pair of mode locked lasers 204 and 205. In the preferred embodiment, the output of upconverter 202 is 100 MHz, and the output of synthesizer 203 is 100.0025 MHz. The mode locked lasers are preferably 780 nm lasers of Calmar Optcom Inc. of Sunnyvale, Calif. The optical spectrum of laser 204 is depicted in FIG. 3A, which depicts a comb of equally spaced frequency components offset from the optical frequency reference by 100 MHz, 200 MHz, 300 MHz, . . . 1000 GHz, 1000.100 GHz, etc. The optical spectrum of laser 205 is depicted in FIG. 3B, which depicts a comb of equally spaced frequency components 100.0025 MHz, 200.005 MHz, 300.0075 MHz, . . . 1000.0025 GHz, 1000.1250025 GHz, etc. In one embodiment, the lasers 204 and 205 may be optically injection locked by a wavelength locked laser 206, whose output is applied to a beam splitter 207, producing separate beams applied to lasers 204 and 205 respectively.

Figure 3C:
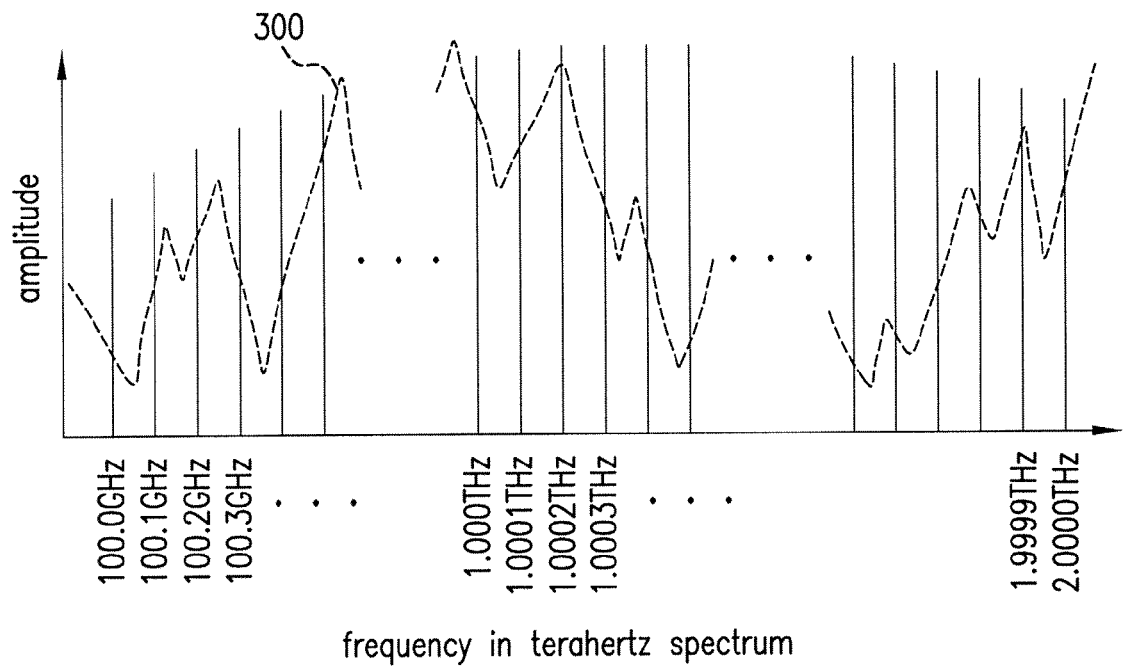

The output 208 of laser 204 is optically amplified 209, which is in turn applied to a lens 210 which focuses the beam to a spot of approximately 10 microns in diameter on the surface of a low temperature grown gallium arsenide photoconductive switch 211. The frequency comb of optical pulses directed to the surface of the PCS semiconductor device produces terahertz radiation in the frequency range 100 GHz to over 2 THz. The terahertz frequency comb spectrum has a fundamental frequency $f_1$ and a series of harmonic components $2f_1, 3f_1, \ldots nf_1 \ldots$ which are integral multiples of the fundamental mode-locked frequency, as depicted in FIG. 3C.

The terahertz radiation emitted from the PCS device 211 is collimated and collected by a silicon lens 213, preferably a hemispherically shaped structure approximately two to three centimeters in diameter. Additional lenses (not shown), composed of Teflon may be placed downstream of the lens 213 to collimate the RF beams into the output THz pulse 214. Beam-shaping mirrors may also be used in lieu of or in addition to the silicon lens 213.

The outgoing terahertz radiation beam is relatively low power, about 1 to 10 microwatts, The target or object 215 to be identified will absorb and transmit some radiation, and also reflect a portion of the radiation back in the direction of the source or user, as shown by the return THz pulse 219. It is estimated that the return power at the receiver antenna should be at least 1 to 10 nanowatts in order for useful signal data to be able to be processed.

For the purpose of the subsequent discussion, we assume that the target 215 has an absorption spectrum as depicted by the dashed line 300 extending over the terahertz frequency spectrum.

On the receiver side, the return signal 219 and the output 216 of the injection-locked laser 205 are combined in the LTG GaAs PCS detector 218 to yield a heterodyne signal. This frequency difference changes from a minimum of 2.5 KHz to a maximum of N times 2.5 KHz, where N is the number of locked modes, and typically the value of N may extend from N=1000 to N=20,000. Due to the extremely wide optical bandwidths of the laser gain media, it is not uncommon for mode-locked lasers to have thousands of locked modes spanning more than 1000 GHz. Therefore it is possible to generate intensity modulation signals over this wide range of frequencies using the technique according to the present invention. The output 216 is directed to a lens 217 which focuses the beam to a ten micron spot on the surface of a LTG GaAs PCS 218 similar to 211 which acts as the detector. The electrical output of the LTG GaAs detector 218 is in the form of electronic RF signals.

Figure 3D:
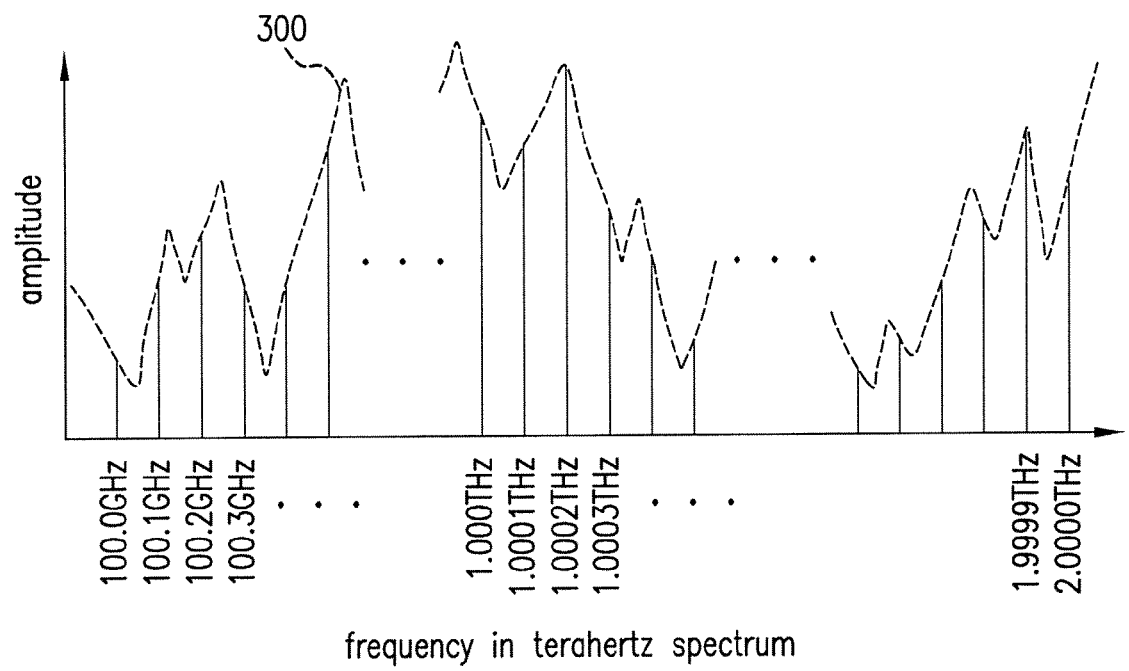

FIG. 3D is a graph illustrating the frequency spectra of the received terahertz RF beam at the detector photoconductive switch according to the present invention reflected from the target 215. It is noted that the return terahertz signal has been attenuated corresponding to the absorption spectrum 300 of the target, thereby providing a terahertz "signature" which may be used to identify the composition of the target.

Figure 3E:
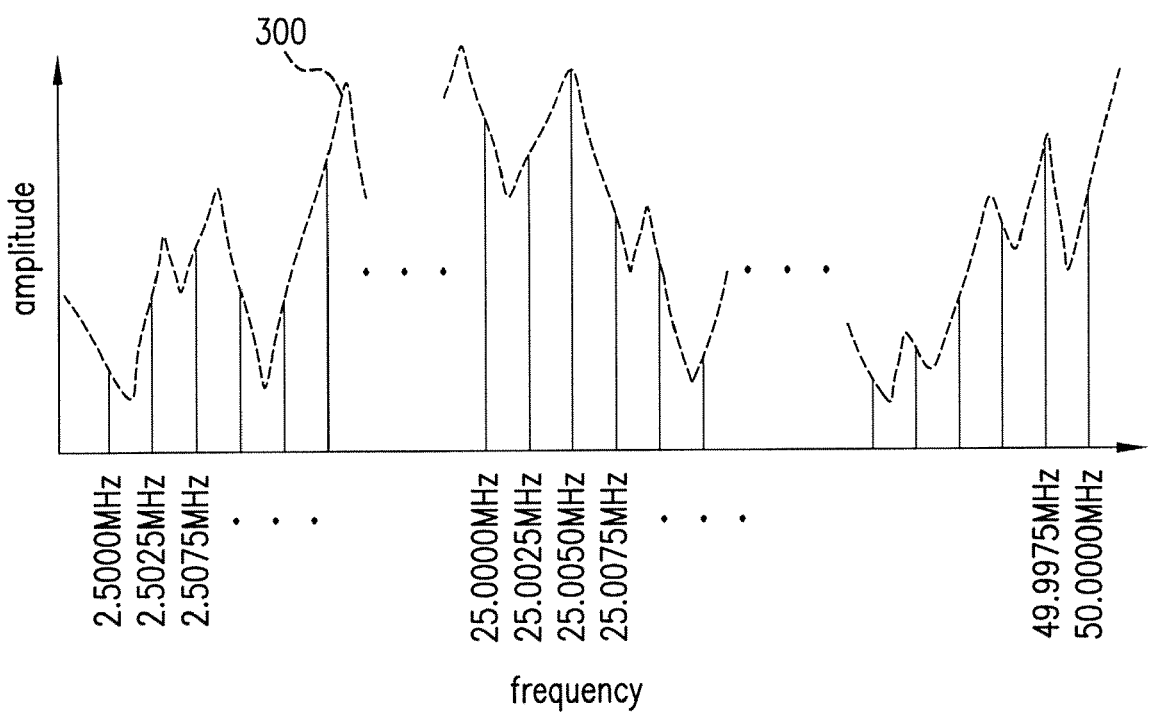

FIG. 3E is a graph illustrating the downconverted spectra in the RF domain which represents the electrical signal output of the PCS detector 218, which occurs upon mixing the received THz signal of FIG. 3D and the applied THz signal of FIG. 3B. The downconverted signal may then be amplified, applied to an analog-to-digital converter, and processed digitally to produce a spectral display or analysis to identify the target or its chemical constituents, as discussed in the prior art references.

Various modifications and improvements of the present invention may also be apparent to those of ordinary skill in the art. Thus, the particular combination of parts described and illustrated herein is intended to represent only certain embodiments of the present invention, and is not intended to serve as limitations of alternate devices within the spirit and scope of the invention.

It will be understood that each of the elements described above, or two or more together, also may find a useful application in other types of constructions differing from the types of constructions described above.

While the invention has been illustrated and described as embodied in a terahertz spectrometer, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

What is claimed is:

1. An apparatus for analyzing, identifying or imaging an object, comprising:
   a first laser providing first predetermined set of optical pulses at a first predetermined set of respective frequencies;
   a source of pulse signals coupled to said first laser and operating in the range of frequencies from 100 GHz to over 2 THz;
   a second laser that provides a second predetermined set of optical pulses at a second predetermined set of respective frequencies where each of the second predetermined set of pulses are different from a respective pulse of the first predetermined set of pulses by a predetermined offset frequency;
   a detector for acquiring spectral information reflected from said object and coupled to the second laser for generating an electrical signal representative of some characteristics of the object; and
   a processor coupled to said detector for processing said electrical signal.

2. An apparatus as defined in claim 1, wherein said source of pulse signals includes a photoconductive switch activated by said first set of optical signals resulting in a radio frequency spectrum f, 2f, 3f, . . . etc. where f is the order of 100 MHz, and said detector includes a photoconductive switch activated by a pulsed laser beam with the frequency spectrum f+Δf, 2(f+Δf), 3(f+Δf), . . . etc. where Δf is of the order of 2.5 KHz.

3. An apparatus as defined in claim 2, further comprising a pair of mode locked lasers for generating the respective set of optical pulses directed to the photoconductive switch.

4. An apparatus as defined in claim 3, wherein said processor determines a characteristic of said object based upon the absorption characteristics of said object in the 100 GHz to over 2 THz frequency band.

5. An apparatus as defined in claim 1, further comprising:
   a first source of pulsed laser optical signals having a time duration of less than one picosecond and being in the frequency range 100 MHz, 200 MHz, etc.; and
   a second source of pulsed laser optical signals, said signals having a set of frequencies offset from the first set of frequency by a constant frequency in the range of n×2.5 KHz, wherein said detector is coupled to said second source of pulse signals to generate a heterodyne electrical signal over the frequency range of said pulse signals.

6. An apparatus as defined in claim 5, wherein said detector is coupled to said second source of pulse signals and generates a heterodyne electrical signal over the frequency range of said pulse signals representative of some characteristics of the object.

7. An apparatus as defined in claim 6, further comprising an oscillator, having an output coupled to a first upconverter having an output coupled to said first source of pulsed lased optical signals, and a second upconverter having an output coupled to said second source of pulsed laser signals.

8. An apparatus as defined in claim 1 wherein said source is a silicon lens.

9. A portable apparatus for analyzing, identifying or imaging an object, comprising:
   a housing capable of being supported by a user;
   a source of pulse signals in said housing;
   a first laser in said housing coupled to said source, said first laser providing a first predetermined set of signals to said source at a first predetermined set of respective frequencies, said pulsed signals from said source being in the range of frequencies from 100 GHz to over 2 THz;
   a lens mounted on said housing for causing said pulsed signals to be focused on said object;
   a second laser in said housing, said second laser providing a second predetermined set of signals at a second predetermined set of frequencies where each of the second predetermined set of signals is different from the first predetermined set by a predetermined offset frequency;
   a detector in said housing for receiving the second set of signals, acquiring spectral information reflected from said object and generating an electrical signal representative of some characteristics of the object; and
   means in said housing coupled to said detector for processing said electrical signal.

10. A method as defined in claim 9 wherein the first and second set of predetermined frequencies each further comprise a respective fundamental frequency and integer multiple of the fundamental frequency.

11. A method as defined in claim 9 wherein the first and second set of predetermined frequencies further comprise combs of equally spaced optical pulses.

12. An apparatus as in claim 9 wherein the provided first predetermined set of signals provided to said source further comprises a spot size of approximately ten microns.

13. An apparatus as in claim 9 wherein said source of pulsed signals further comprises an antenna structure that couples the THz pulses into free space radiation.

14. A method of identifying or imaging an object comprising the steps of:
    simultaneously transmitting a first predetermined spectral pattern of pulse signals to an object, said signals being in the range of frequencies from 100 GHz to over 2 THz said spectral pattern being generated by the interaction of a first predetermined set of signals at a first predetermined set of respective frequencies with a photoconductive switch;
    detecting return signals in said range after propagation through or reflection from said object by utilizing a second photoconductive switch tuned to a second predetermined spectral pattern of pulse signals wherein the first and second predetermined patterns of pulsed signals each further comprise a respective fundamental frequency and integral multiple of the fundamental frequency and each pulse signal of said second predetermined pattern is shifted by a small amount from the corresponding pulse signal in said first set of signals of said spectral pattern; and
    analyzing said spectral information to identify said object or a compositional characteristic thereof.

15. A method for analyzing, identifying or imaging an object, comprising:
    providing a first predetermined set of optical signals at a first predetermined set of respective frequencies;
    generating a source of pulsed signals in the range of frequencies from 100 GHz to over 2 THz from the first predetermined set of optical signals;
    focusing said pulsed signals on said object;
    generating a second predetermined set of optical signals at a second predetermined set of respective frequencies where each of the second predetermined set of signals are different from a respective signal of the first predetermined set of signals by a predetermined offset frequency;
    combining the return signals received from the object with the second predetermined set of signals in a detector; and
    processing the combined signals.

16. A method as defined in claim 15 wherein the signal received from the object is a reflected signal.

17. A method as defined in claim 15 wherein the first predetermined set of respective frequencies comprises a comb of equally spaced pulses.

18. A method as defined in claim 17, wherein the pulses are centered at frequencies of approximately 100 MHz, 200 MHz, 300 MHz, . . . 1000 GHz, 1000.100 GHz, etc.

19. A method as defined in claim 15 wherein the second predetermined set of respective frequencies further comprise a comb of equally spaced pulses centered at approximately 100.0025 MHz, 200.005 MHz, etc.

20. A method of analyzing, identifying or imaging an object as in claim 15 wherein the step of generating a first and second predetermined sets of signals further comprises applying a predetermined low frequency electrical signal to first and second upconverters where the first and second upconverters have respective output frequencies that differ by the offset frequency.

21. A method of analyzing, identifying or imaging an object as in claim 20 further comprising generating the first set of predetermined signals by coupling an output of the first upconverter to a first mode locked laser.

22. A method of analyzing, identifying or imaging an object as in claim 21 further comprising generating the second set of predetermined signals by coupling an output of the second upconverter to a second mode locked laser.

23. A method of analyzing, identifying or imaging an object as in claim 22 further comprising coupling an optical signal from a wavelength locked laser to excite the first and second mode locked lasers.

24. An apparatus for analyzing, identifying or imaging an object, comprising:
    a first optical source that provides a first comb of equally spaced optical pulses;
    a second optical source that provides a second comb of equally spaced optical pulses with each optical pulse of the second comb offset from a respective pulse of the first comb by a predetermined offset frequency;
    a radiator that receives the first comb of pulses and produces target interacting pulsed signals in the range of frequencies of from 100 GHz to over 2 THz;
    a detector that combines the target interacted pulsed signals with the second comb to produce an electrical signal; and
    a processor coupled to said detector that processes the electrical signal.

25. An apparatus as in claim 24 wherein each of the pulses of the first and second comb have a duration of less than one picosecond.

26. An apparatus as in claim 25 wherein the pulses of the first and second comb have an inter-pulse spacing of approximately ten nanoseconds.

27. An apparatus as in claim 25 wherein the first comb of pulses are centered at frequencies of approximately 100 MHz, 200 MHz, 300 MHz, . . . 1000 GHz, 1000.100 GHz, etc.

28. An apparatus as in claim 25 wherein the second comb of pulses are centered at frequencies of approximately 100.0025 MHz, 200.005 MHz, 300.0075 MHz, . . . 1000.0025 GHz, 1000.1250025 GHz, etc.

29. A method for analyzing, identifying or imaging a target comprising:
    providing first and second lasers for producing a respective first and second composite output beam in an integrated module wherein respective spectral components of the first and second composite beams are different from each other and wherein each further comprise a respective fundamental frequency and integer multiple of the fundamental frequency;
    producing continuous wave signals in the range of frequencies from 100 GHz to over 2 THz by a first photoconductive switch activated by said first composite optical beam;
    simultaneously focusing said signals on or through said target; and
    acquiring spectral information reflected from or transmitted through said target by a detector and coupled to said second composite optical beam for generating an electrical signal representative of some characteristic of the target.

30. A method for analyzing, identifying or imaging an object, comprising:
    providing a first predetermined set of optical signals at a first predetermined set of respective frequencies;
    generating a source of pulsed signals in the range of frequencies from 100 GHz to over 2 THz from the first predetermined set of optical signals;
    directing said pulsed signals on said object;
    generating a second predetermined set of optical signals at a second predetermined set of respective frequencies;

mixing the return signals received from the object with the second predetermined set of signals in a herterodying downconverter to produce a downconverted frequency set of signals; and processing the downconverted signals to determine an aspect of the object.

31. A method as defined in claim 30, further comprising processing said downconverted signal to determine a characteristic of said object based upon the absorption characteristic of said object in the 100 GHz to over 2 THz frequency band.

32. A method for analyzing, identifying or imaging an object, comprising:

providing a first predetermined set of optical signals at a first predetermined set of respective frequencies;

generating a source of pulsed signals in the range of frequencies from 100 GHz to over 2 THz from the first predetermined set of optical signals;

directing said pulsed signals on said object;

generating a second predetermined set of optical signals at a second predetermined set of respective frequencies;

mixing the return signals received from the object with the second predetermined set of signals in a heterodyne downconverter to produce a downconverted frequency set of signals; and processing the downconverted signals to determine an aspect of the object.

33. A method for analyzing, identifying or imaging an object, comprising:

providing a first predetermined set of optical signals at a first predetermined set of respective frequencies;

generating a source of pulsed signals in the range of frequencies from 100 GHz to over 2 THz from the first predetermined set of optical signals;

simultaneously directing said pulsed signals on said object;

generating a second predetermined set of optical signals at a second predetermined set of respective frequencies; and combining the simultaneous return signals received from the object with the second predetermined set of signals in a detector to simultaneously determine the absorption characteristics of the object over a plurality of frequencies.

34. An apparatus for analyzing, identifying or imaging an object, comprising:

a source of pulse signals in the range of frequencies from 100 GHz to over 2 THz substantially simultaneously directed to said object; and a detector for acquiring spectral information reflected from said object and performing a heterodyne downconversion for generating an electrical signal representative of some characteristics of the object.

35. An apparatus as defined in claim 34, wherein said source of pulse signals includes a photoconductive switch activated by a pulsed laser beam resulting in a radio frequency spectrum f, 2f, 3f, . . . etc. where f is the order of 100 MHz, and said detector includes a photoconductive switch activated by a pulsed laser beam with the frequency spectrum f+$\Delta$f, 2(f+$\Delta$f), 3(f+$\Delta$f), . . . etc. where $\Delta$f is of the order of 2.5 KHz.

36. An apparatus as defined in claim 35, further comprising a pair of mode locked lasers for generating the respective pulsed laser beams directed to the photoconductive switch.

37. An apparatus as defined in claim 35, further comprising a processor for analyzing said electrical signal and determining a characteristic of said object based upon the absorption characteristics of said object in the 100 GHz to over 2 THz frequency band.

38. An apparatus as defined in claim 34, further comprising:

a first source of pulsed laser optical signals, said signals being in the range of frequencies from 100 GHz to over 2 THz; and a second source of pulsed laser optical signals, said signals having a set of frequencies offset from the first set of frequency by a constant frequency in the range of n×2.5 KHz.

* * * * *